(12) United States Patent
Fitzgerald

(10) Patent No.: US 10,548,698 B2
(45) Date of Patent: Feb. 4, 2020

(54) TEETH CLEANING TRAVEL KIT

(71) Applicant: Brenda Fitzgerald, Bethel, OH (US)

(72) Inventor: Brenda Fitzgerald, Bethel, OH (US)

(73) Assignee: Brush LLC, Cincinnati, OH (US)

(*) Notice: Subject to any disclaimer, the term of this patent is extended or adjusted under 35 U.S.C. 154(b) by 0 days.

(21) Appl. No.: 15/543,589

(22) PCT Filed: Jan. 13, 2016

(86) PCT No.: PCT/US2016/013293
§ 371 (c)(1),
(2) Date: Jul. 14, 2017

(87) PCT Pub. No.: WO2016/115276
PCT Pub. Date: Jul. 21, 2016

(65) Prior Publication Data
US 2017/0367801 A1   Dec. 28, 2017

Related U.S. Application Data

(60) Provisional application No. 62/103,293, filed on Jan. 14, 2015.

(51) Int. Cl.
*A61C 17/22* (2006.01)
*A61C 19/06* (2006.01)
*A61C 17/16* (2006.01)

(52) U.S. Cl.
CPC ............ *A61C 17/228* (2013.01); *A61C 17/16* (2013.01); *A61C 19/063* (2013.01)

(58) Field of Classification Search
CPC ......... A61C 17/00; A61C 17/16; A61C 17/22; A61C 17/222; A61C 17/228; A61C 17/32; A61C 19/063; A46B 9/04; A46B 9/045; A46B 11/003; A46B 11/002; A46B 11/0062; A46B 11/0075
See application file for complete search history.

(56) References Cited

U.S. PATENT DOCUMENTS

| 3,769,652 A | * | 11/1973 | Rainer | A46B 9/045 15/167.2 |
| 5,938,445 A | * | 8/1999 | Kodama | A61F 5/56 128/861 |
| 6,062,233 A | * | 5/2000 | Williams | A45D 44/18 132/308 |

(Continued)

*Primary Examiner* — Nicholas J. Weiss
(74) *Attorney, Agent, or Firm* — Jenei LLC

(57) ABSTRACT

A teeth cleaning travel kit includes toothbrushing mouthpiece that has two inverted channels dimensioned to receive upper and lower bites of dental arches of a user, the channels being integral with one another. Teeth-cleaning bristles inwardly project within the two inverted channels to bear inwardly against teeth and gums of the user, wherein the channels and teeth-cleaning bristles are configured such that mastication produces relative brushing movement of the teeth-cleaning bristles over the teeth and gums. An oral hygiene promoting product is attached to one of the two inverted channels and the teeth-cleaning bristles that is released by action of the user's mouth. The teeth cleaning travel kit also includes a vessel that contains a rinsing fluid and kit packaging that contains the toothbrushing mouthpiece and vessel.

12 Claims, 5 Drawing Sheets

(56) References Cited

U.S. PATENT DOCUMENTS

| | | | | |
|---|---|---|---|---|
| 6,299,441 B1* | 10/2001 | Novak | ................. | A63J 7/00 |
| | | | | 128/861 |
| 8,292,624 B2* | 10/2012 | Gallagher, Jr. | .... | A46B 11/0003 |
| | | | | 433/216 |
| 8,900,614 B2* | 12/2014 | Bardach | ............... | A61F 5/0006 |
| | | | | 424/422 |
| 9,173,476 B2* | 11/2015 | Minano Fernandez | ..................... | |
| | | | | A46B 9/045 |
| 9,526,597 B2* | 12/2016 | Steur | .................. | A61C 17/222 |
| 9,986,819 B2* | 6/2018 | Flynn | ................ | A46B 11/0006 |
| 2010/0143863 A1* | 6/2010 | Lin | ....................... | A61C 17/20 |
| | | | | 433/87 |
| 2014/0014543 A1* | 1/2014 | Hohlbein | .......... | A46B 11/0003 |
| | | | | 206/368 |
| 2016/0206415 A1* | 7/2016 | Kraft | ................. | A61C 17/20 |

* cited by examiner

TEETH CLEANING TRAVEL KIT

PRIORITY AND CROSS-REFERENCE TO RELATED APPLICATIONS

The present application is a § 371 national entry of International Patent Application No. PCT/US16/13293 to Fitzgerald, filed 13 Jan. 2016, entitled "TEETH CLEANING TRAVEL KIT", and which claims the benefit of priority to U.S. Patent Provisional Application No. 62/103,293, entitled "TEETH CLEANING TRAVEL KIT" filed Jan. 14, 2015, the disclosures of which are incorporated herein by reference in their entirety.

BACKGROUND OF THE INVENTION

Field of the Invention

The field of art disclosed herein pertains to devices that promote dental hygiene and more particularly to mouthpieces shaped to enclose the teeth for cleaning.

Description of the Related Art

Generally, toothbrushes on a handle are used to clean a person's teeth. Given the relatively small surface area of the head of the toothbrush, a considerable amount of time is required to effectively brush all of the teeth surfaces. Typically a sink is required to perform the necessary rinsing at the conclusion of teethbrushing. For these and other reasons, many people forgo brushing as recommended due to the inconvenience or infeasibility.

BRIEF DESCRIPTION OF THE FIGURES

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

The present disclosure provides in one aspect a teeth cleaning travel kit having a toothbrushing mouthpiece having two inverted channels dimensioned to receive upper and lower bites of dental arches of a user, the channels being integral with one another. Teeth-cleaning bristles inwardly project within the two inverted channels to bear inwardly against teeth and gums of the user. The channels and teeth-cleaning bristles are configured such that mastication produces relative brushing movement of the teeth-cleaning bristles over the teeth and gums. An oral hygiene promoting product is attached to one of the two inverted channels and the teeth-cleaning bristles that is released by action of the user's mouth. The teeth cleaning travel kit includes a vessel contains a rinsing fluid and kit packaging that contains the toothbrushing mouthpiece and vessel.

Turning now to the Drawings, the detailed description set forth below in connection with the appended drawings is intended as a description of various configurations and is not intended to represent the only configurations in which the concepts described herein may be practiced. The detailed description includes specific details for the purpose of providing a thorough understanding of various concepts with like numerals denote like components throughout the several views. However, it will be apparent to those skilled in the art that these concepts may be practiced without these specific details. In some instances, well known structures and components are shown in block diagram form in order to avoid obscuring such concepts.

Figure 1:
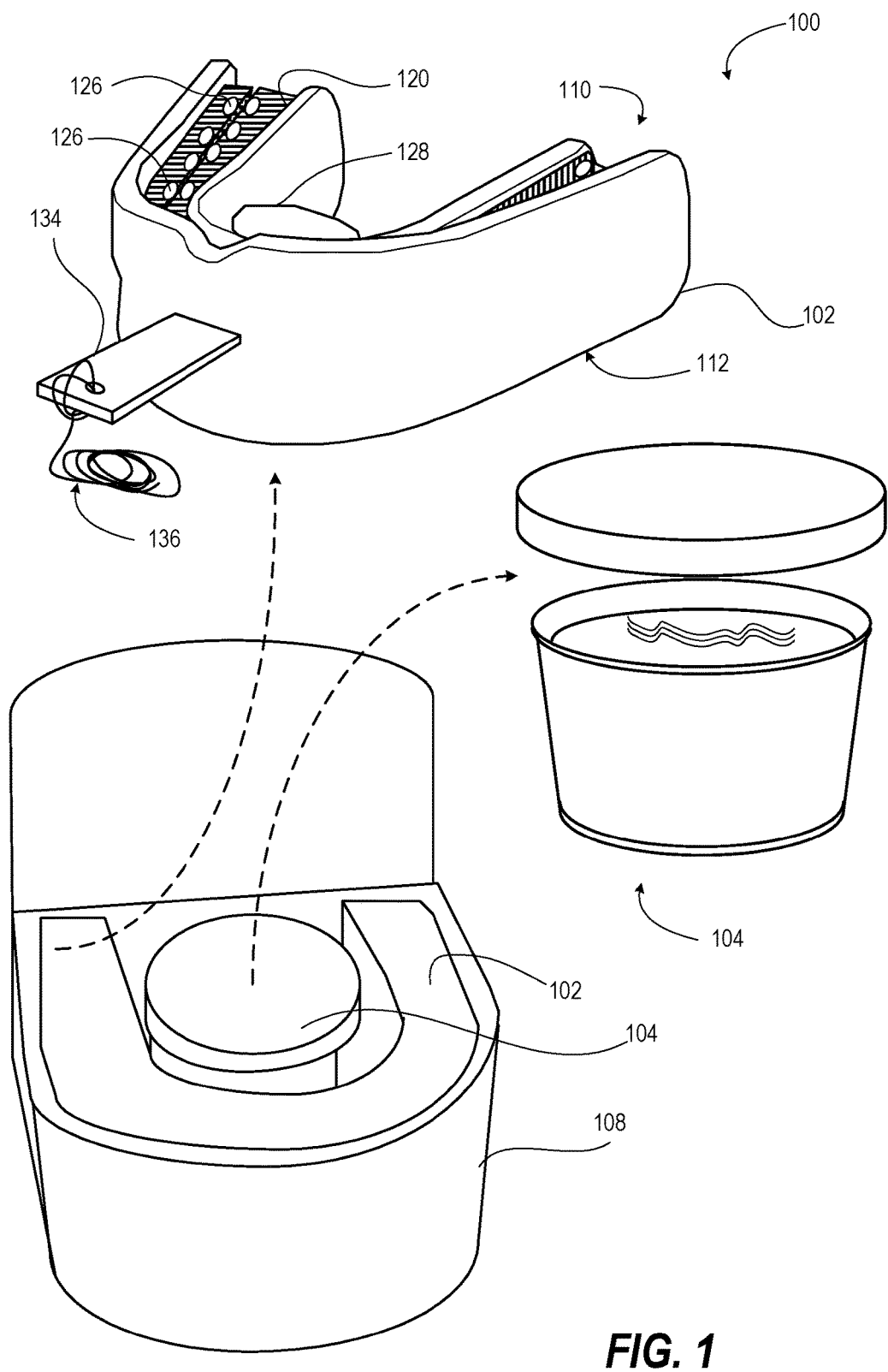
FIG. 1 illustrates a perspective view of a teeth cleaning travel kit for brushing teeth on the go, according to one or more embodiments.
Figure 2:
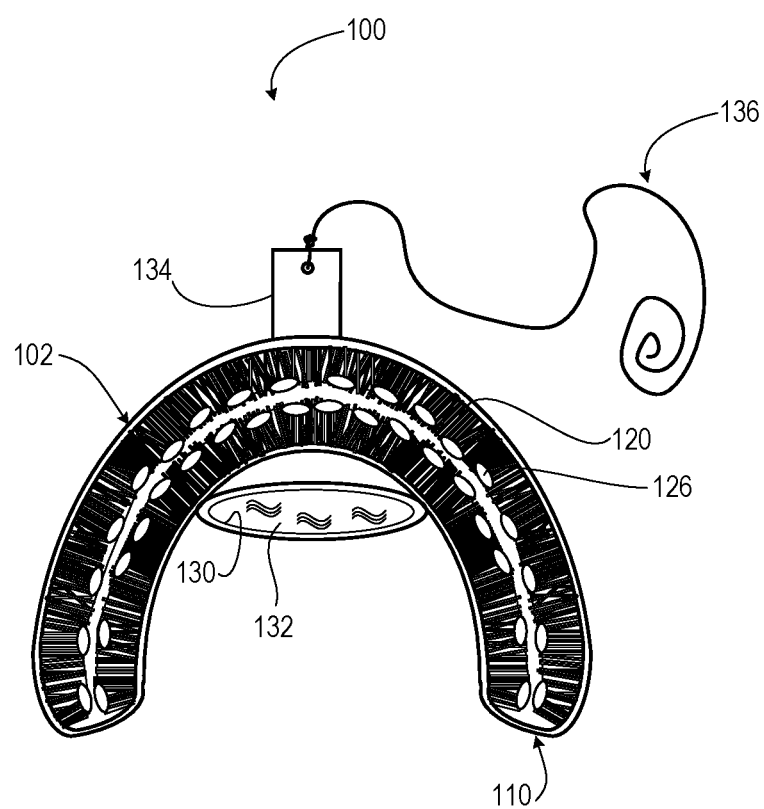
FIG. 2 illustrates a top view of a toothbrush mouthpiece of the teeth cleaning travel kit of FIG. 1, according to one or more embodiments.
Figure 3:
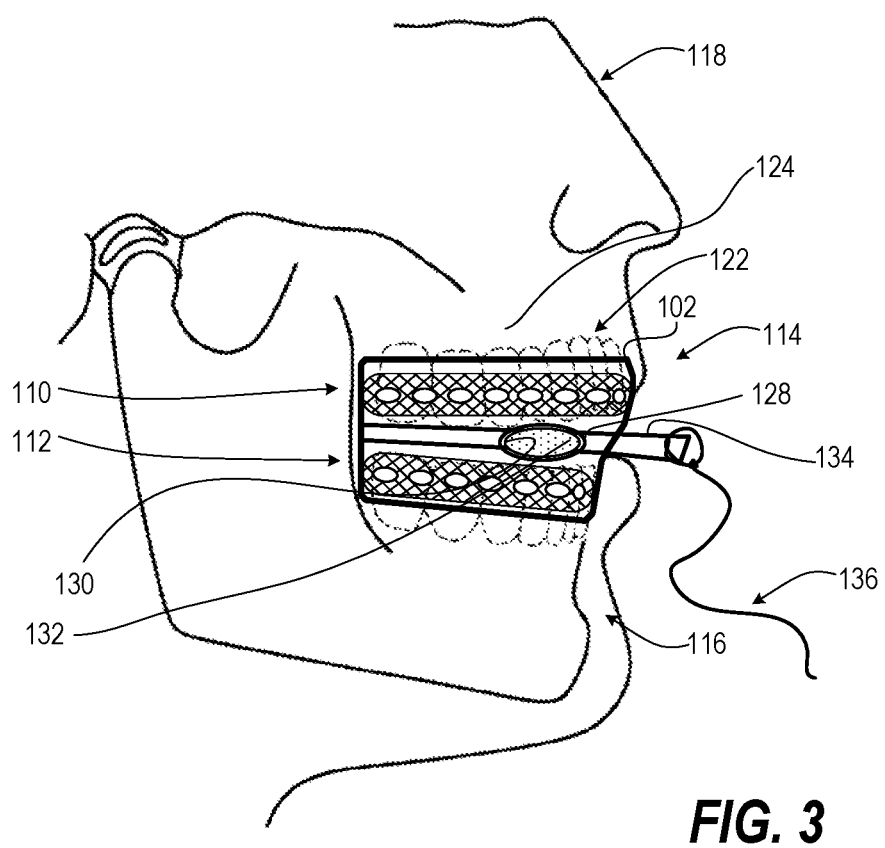
FIG. 3 illustrates a side cutaway view of a user with the toothbrush mouthpiece inserted into his mouth, according to one or more embodiments.
Figure 4:
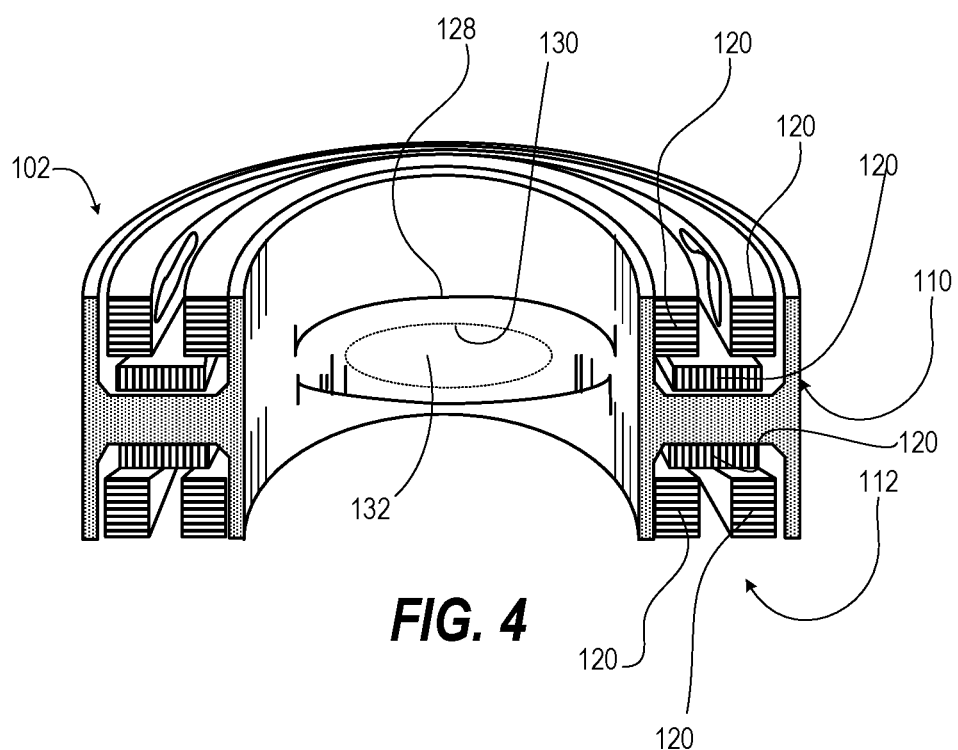
FIG. 4 illustrates a rear perspective view of the toothbrush mouthpiece of FIG. 1, according to one or more embodiment.

FIGS. 1-4 illustrate a teeth cleaning travel kit 100 includes a toothbrushing mouthpiece 102, a sealed cup 104 containing water 106 as a rinsing vessel, and kit packaging 108. The toothbrushing mouthpiece 102 includes two inverted channels 110, 112 dimensioned to receive upper and lower bites 114, 116 of dental arches of a user 118 (FIG. 3). The channels 110, 112 can be integral with one another. With particular reference to FIG. 4, teeth-cleaning bristles 120 inwardly projecting within the two inverted channels 110, 112 on three sides to bear inwardly against teeth 122 and gums 124 of the user 118 (FIG. 3). The channels 110, 112 and teeth-cleaning bristles 120 are configured such that mastication produces relative brushing movement of the teeth-cleaning bristles 120 over the teeth 122 and gums 124.

In accordance with one aspect of this invention the cleaning elements may be in the form of bristles made from conventional materials, such as nylon, as well as from a combination of materials so as to provide the proper stiffness in an economical manner. For example, the cleaning elements could be made of a flexible resilient material, such as TPE and a lesser expensive material such as LLDPE (linear low density polyethylene) or EVA (ethylene vinyl acetate) or a TPE. The cleaning elements could be made of a blend of TPE and either LLDPE, EVA, or polypropylene. Preferably, the two materials are combined to provide a stiffness of less than 600 MPa. The blend of materials would give the properties of conventional nylon bristles, while offering reduced costs. For example, there would be lower manufacturing costs by injection molding instead of conventional bristle tufting. Alternatively the resilient material could be a single material, such as hard TPE, straight LLDPE or straight EVA.

In one embodiment of the invention, the cleaning elements could be hollow, such as hollow bristles, which are capable of absorbing a medicament by capillary action. Such practice of the invention would be particularly useful for children where a medicament or some form of flavor could be dispensed from the hollow cleaning elements. It is also possible to leach antibacterial material from the cleaning elements. In one practice of the invention where the cleaning elements are used to dispense oral care materials the cleaning elements themselves may be considered as the oral care dispensers without requiring additional dispensers such as gel capsules.

An oral hygiene promoting product is attached to one of the two inverted channels 110, 112 and the teeth-cleaning bristles 120 that is released by action of the user's mouth. In an exemplary embodiment, two oral hygiene promoting products are attached for different uses by different actuation processes. First, toothpaste nodules 126 are adhered to the teeth-cleaning bristles 120. For example, the toothpaste nodules 126 can be toothpaste power, dried toothpaste, encapsulated toothpaste, packed toothpowder, tooth cleaning gel dentifrice, baking soda mixture, etc. Any suitable oral care products could be dispensed from the teeth-cleaning bristles 120. Such products include, but are not limited to the gel capsules and strips and could contain toothpaste, tooth powder or could be a mouthwash gel, powder or liquid. The materials could be flavored and could be provided in sets of different flavors and/or different characteristics such as medicaments, numbing materials, etc.

Second, a lateral brace 128 attached across lateral sides of one of the two inverted channels 110, 112 provides a means for the user to position the toothbrushing mouthpiece 102 with the tongue. The lateral brace 128 also contains a rupturable reservoir 130 containing a oral hygiene promoting product, specifically a fluoride mouthwash 132.

The toothbrushing mouthpiece 102 can include a handle 134 and/or a length of dental floss 136 to assist in withdrawing the mouthpiece. The dental floss 136 can also be used for flossing the teeth 122.

The bristles, the mouthpiece, and the handle can be transparent or white in color, or they can have a variety of different colors. Part or all of the bristles can be perpendicular to the mouthpiece. Part or all of the bristle can also be angular to the mouthpiece. The bristle can be arranged both perpendicularly and angularly to the mouthpiece.

The bristle can be arranged in a variety of different patterns. The patterns can include bundles of bristles in rows, bundles of bristles in circular shapes, bundles of bristles in round shapes, bundles of bristles in jagged shapes, bundles of bristles in cylindrical shapes, bundles of bristles in cubical shapes, bundles of bristles in ring shapes, evenly spaced bristles in bundles, evenly spaced bundles of bristles, and so on. The bristles can be separated from one another by about 0 to 4 millimeters. The bundles having a size about 1 square millimeter to 2 square inches. The bundles comprise 1 to a few hundred bristles. And the bundles are separated from one another by about 0 to 5 millimeters.

The bristles of the mouthpiece can be made of synthetic and/or natural fibers. Synthetic fibers include but are not limited to bio-plastic, plastic, nylon, polyester, and/or acrylic. Natural fibers include but are not limited to animal and plant fibers, including rubber, wood, and bamboo. It should be noted that biodegradable materials can also be used.

The bristles, the mouthpiece, and the handle can be created with or without the addition of flavoring ingredients. The flavors include natural flavors and artificial flavors. The flavors can include one or more flavors of the fruits, plants, herbs, teas, roots, flowers, nuts, vegetables, beans, cereals, vegetable skins, fruit skins, and other flavors, including artificial sweeteners, vinegar, sugar, syrup, honey, menthol, echinacea, elder, horehound, mallow, sage, thyme, cowslip, burnet, yarrow, marshmallow, lady's mantle, speedwell, plantain, linden flowers, wild thyme, hyssop, eucalyptus, sea buckthorn, elder blossom, verbena, lemon balm, clove, coriander, cumin, basil, dill, rosemary, parsley, carob, fennel, oregano, nutmeg, allspice, catnip, wormwood, musk, pepper, chili, horseradish, tumeric, mustard, curry, wasabi, mountain mint, lemon grass, peppermint, spearmint, wintergreen, ginger, ginseng, garlic, truffle, chive, cinnamon, licorice, rose, earl grey, darjeeling, chrysanthemum, jasmine, chamomile, lavender, acacia, safflower, vanilla, almond, apple, orange, lemon, lime, grapefruit, grape, guava, plum, peach, pear, blackberry, blueberry, strawberry, cranberry, raspberry, cherry, mango, pineapple, pomegranate, papaya, watermelon, honeydew, coconut, durian, passion fruit, banana, fig, apricot, mandarin, blackcurrant, starfruit, kiwi, pomelo, lychee, loquat, persimmon, tangerine, mangosteen, noni, sugar apple, mulberry, elderberry, gooseberry, lingonberry, juniper berry, jackfruit, dragonfruit, butter, peanut butter, cheese, butterscotch, caramel, chocolate, coffee, green tea, roasted grain beverage, potato, taro, carrot, turnip, yam, parsnip, rutabaga, burdock, radish, sweet potato, lotus root, beet root, parsley root, cucumber, squash, zucchini, pumpkin, eggplant, pepper, tomato, avocado, winter melon, bitter melon, tomatillo, chayote, okra, breadfruit, pod, broccoli, cauliflower, globe antichoke, caper, asparagus, bamboo shoot, celery, rhubarb, cardoon, Chinese celery, Kohlrabi, galangal, cabbage, kale, collard green, spinach, arugula, beet green, bok choy, chard, choi sum, turnip green, endive, lettuce, mustard green, watercress, gai lan, leek, onion, shallot, rice, corn, wheat, barley, oat, rye, almond, cashew, chestnut, coconut, hazelnut, macademia, peanut, pecan, pine nut, pistachio, walnut, acorn, brazil nut, green bean, white bean, yellow bean, pinto bean, soybean, lima bean, kidney bean, pea bean, mung bean, chickpea, snow pea, lentil, seaweed, sea grape, mushroom, brussels sprout, bean sprout, urad, alfalfa, fennel, dandelion, and so on. Other herb flavors include ajwain, akudjura, alexanders, alkanet, alligator pepper, allspice, angelica, anise, anise hyssop, aniseed myrtle, annatto, apple mint, artemisia, asafoetida, asarabacca, avens, avocado leaf, barberry, bay leaf, bee balm, boldo, borage, black cardamom, blue fenugreek, caraway, cardamom, cassia, cayenne pepper, celery leaf, celery seed, chervil, chicory, cicely, cilantro, clary, costmary, cubeb pepper, cudweed, culantro, curry leaf, curry plant, dill seed, epazote, fenugreek, file powder, fingerroot, galangal, galingale, golpar, grains of paradise, grains of selim, houttuynia cordata, huacatay, Indonesian bay leaf, jimbu, juniper berry, kaffir lime leaves, kala zeera, kawakawa seeds, kencur, keluak, kinh gioi, kokam seed, korarima, koseret leaves, lemon myrtle, lemon ironbark, lemon verbena, leptotes bicolor, lesser calamint, lime flower, lovage, mahlab, marjoram, mastic, mountain horopito, musk mallow, nasturtium, nigella, njangsa, neem, olida, orris root, pandan flower, pandan leaf, paprika, paracress, peppermint gum leaf, perilla, pandanus amaryllifolius, quassia, ramsons, rice paddy herb, rue, saffron, salad burnet, salep, sassafras, savory, silphium, shiso, sorrel, spikenard, star anise, sumac, sweet woodruff, tarragon, voatsiperifery, water-pepper, watercress, wattleseed, wild betel, willow herb, wood avens, woodruff, and so on. The comprised flavoring ingredients can be imbedded and/or coated.

The bristles, the mouthpiece, and the handle can be created with or without the addition of nutritional ingredients. The nutritional ingredients may include one or more of various essential nutrients, including vitamins, dietary minerals, amino acids, and fatty acids. The vitamins include vitamin A, vitamin B1, vitamin B2, vitamin B3, vitamin B5, vitamin B6, vitamin B7, vitamin B9, vitamin B12, vitamin C, vitamin D, vitamin E, and vitamin K. The dietary minerals include calcium, phosphorus, potassium, sulfur, sodium, chlorine, magnesium, iron, cobalt, copper, zinc, molybdenum, iodine, selenium, manganese, nickle, chromium, fluorine, boron, and strontium. The amino acids include histidine, isoleucine, leucine, lysine, methionine, cysteine, phenylalanine, tyrosine, threonine, tryptophan, and valine. The fatty acids include alpha-linolenic acid (an omega-3 fatty acid) and linoleic acid (an omega-6 fatty acid). The comprised nutritional ingredients can be imbedded and/or coated.

The bristles, the mouthpiece, and the handle can be created with or without the addition of cleansing ingredients. The cleansing ingredients may include one or more of toothpaste, baking soda, fluoride, triclosan, bleach, salt, Epsom salt, charcoal, and so on. The comprised cleansing ingredients can be imbedded and/or coated. The toothpaste can also be applied on top of the bristles or can be embedded thereon.

In some possible embodiments, different mouthpieces may be available that contain different oral care agents or formulations (e.g. whitening, enamel protection, anti-sensitivity, flavors, etc.). The mouthpiece may be color-coded and/or include indicia to correspond with a particular type of oral care agent formulation contained inside. This would allow the user to quickly identify which formulation is presently contained in the oral hygiene promoting product. Such different type oral hygiene promoting products may be included in a kit as already described herein.

Figure 5:
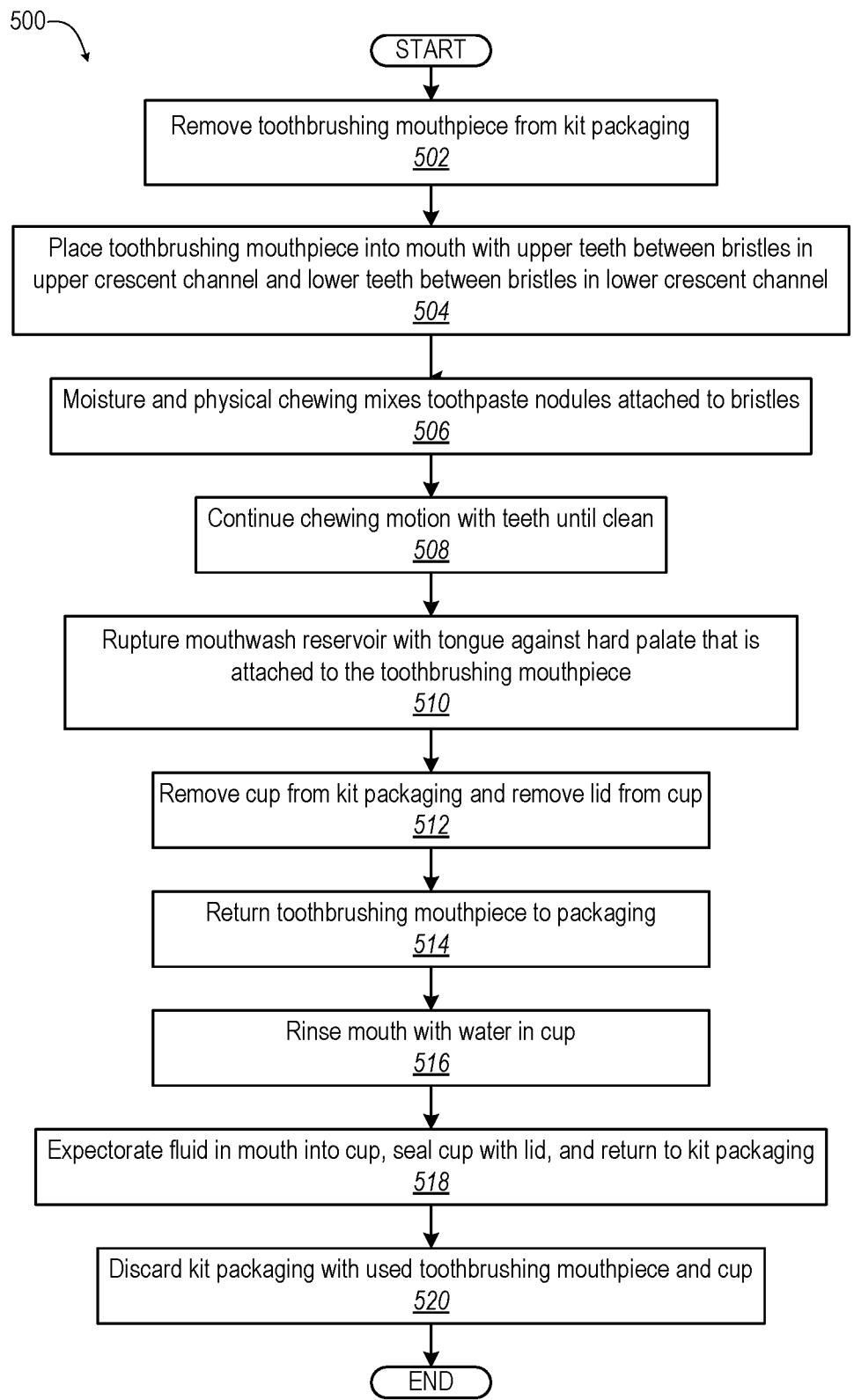
FIG. 5 illustrates a flow diagram of a method of using the teeth cleaning travel kit, according to at least one embodiment method.

FIG. 5 illustrates a method 500 for cleaning teeth on the go. In one embodiment, the method 500 includes removing the toothbrushing mouthpiece from kit packaging (block 502). The method 500 includes placing toothbrushing mouthpiece into mouth with upper teeth between bristles in the upper crescent channel and the lower teeth between bristles in the lower crescent channel (block 504). The method 500 includes physical chewing of the toothbrushing mouthpiece to moisten toothpaste nodules attached to the bristles (block 506). The user continues chewing motion until teeth are clean (block 508). Then, the user can rupture a mouthwash reservoir with tongue against hard palate (block 510). The reservoir can be attached as a lateral brace that also assists in maintaining the mouthpiece in place during chewing. Alternatively, a reservoir trapped in the mouthpiece between the teeth can be ruptured by a hard bite. The user can remove a cup from kit packaging and remove a lid from the cup (block 512). The user removes the toothbrushing mouthpiece to packaging for later cleaning and reuse or for disposal (block 514). The user rinses his mouth with water from the cup (block 516). The user can use the cup to expectorate fluid in the mouth back into the cup, seal the cup, and return the sealed up to the kit packaging (block 518). Then, the user can discard the kit packaging along with the used toothbrushing mouthpiece and sealed cup (block 520).

In the above described flow chart, one or more of the methods may be embodied in a computer readable device containing computer readable code such that a series of functional processes are performed when the computer readable code is executed on a computing device. In some implementations, certain steps of the methods are combined, performed simultaneously or in a different order, or perhaps omitted, without deviating from the scope of the disclosure. Thus, while the method blocks are described and illustrated in a particular sequence, use of a specific sequence of functional processes represented by the blocks is not meant to imply any limitations on the disclosure. Changes may be made with regards to the sequence of processes without departing from the scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, such as a service processor, or other programmable data processing apparatus to produce a machine, such that the instructions, which execute via the processor of the computer or other programmable data processing apparatus, performs the method for implementing the functions/acts specified in the flowchart and/or block diagram block or blocks.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A teeth cleaning travel kit comprising:
   a toothbrushing mouthpiece comprising:
      two inverted channels dimensioned to receive upper and lower bites of dental arches of a user, the channels being integral with one another;
      teeth-cleaning bristles inwardly projecting within the two inverted channels to bear inwardly against teeth and gums of the user, wherein the channels and teeth-cleaning bristles are configured such that mastication produces relative brushing movement of the teeth-cleaning bristles over the teeth and gums; and
      a rupturable reservoir containing an oral hygiene promoting product, attached to at least one of the two inverted channels, and positioned in a selected one of: (i) between a tongue and a hard palate of the user; and (ii) trapped between teeth of the user enabling in mouth rupturing and dispensing of the oral hygiene promoting product from the rupturable reservoir by action of the user's mouth;
   a vessel that contains a rinsing fluid; and
   kit packaging that contains the toothbrushing mouthpiece and vessel.

2. The teeth cleaning travel kit of claim 1, wherein the toothbrushing mouthpiece further comprises a lateral brace connecting lateral sides of at least one of the channels, wherein the lateral brace is placed such that pressure from a tongue of the user in a direction toward one of the bites during said mastication holds the toothbrushing mouthpiece in place against said one of the bites, while the teeth-cleaning bristles brush over the other of the bites, wherein the lateral brace comprises the rupturable reservoir containing the oral hygiene promoting product.

3. The teeth cleaning travel kit of claim 2, wherein the oral hygiene promoting product comprises mouthwash.

4. The teeth cleaning travel kit of claim 1, further comprising toothpaste adhered to the teeth-cleaning bristles.

5. A toothbrushing mouthpiece comprising:
   two inverted channels dimensioned to receive upper and lower bites of dental arches of a user, the channels being integral with one another;
   teeth-cleaning bristles inwardly projecting within the two inverted channels to bear inwardly against teeth and gums of the user, wherein the channels and teeth-cleaning bristles are configured such that mastication produces relative brushing movement of the teeth-cleaning bristles over the teeth and gums; and
   a rupturable reservoir containing an oral hygiene promoting product, attached to at least one of the two inverted channels, and positioned in a selected one of: (i) between a tongue and a hard palate of the user; and (ii) trapped between teeth of the user enabling in mouth rupturing and dispensing of the oral hygiene promoting product from the rupturable reservoir by action of the user's mouth.

6. The toothbrushing mouthpiece of claim 5, further comprising a lateral brace connecting lateral sides of at least one of the channels, wherein the lateral brace is placed such that pressure from a tongue of the user in a direction toward one of the bites during said mastication holds the toothbrushing mouthpiece in place against said one of the bites, while the teeth-cleaning bristles brush over the other of the bites, wherein the lateral brace comprises the rupturable reservoir containing the oral hygiene promoting product.

7. The toothbrushing mouthpiece of claim 6, wherein the oral hygiene promoting product comprises mouthwash.

8. The toothbrushing mouthpiece of claim 5, further comprising toothpaste adhered to the teeth-cleaning bristles.

9. The teeth cleaning travel kit of claim 1, further comprising a length of dental floss attached to the toothbrushing mouthpiece and usable for both extracting the toothbrushing mouthpiece from the mouth and for flossing teeth.

10. The toothbrushing mouthpiece of claim 5, further comprising a length of dental floss attached to the toothbrushing mouthpiece and usable for both extracting the toothbrushing mouthpiece from the mouth and for flossing teeth.

11. The teeth cleaning travel kit of claim 1, wherein the rupturable reservoir is positioned between the two inverted channels between the teeth of the user.

12. The toothbrushing mouthpiece of claim 5, wherein the rupturable reservoir is positioned between the two inverted channels between the teeth of the user.

* * * * *